United States Patent
Lee et al.

(10) Patent No.: US 10,130,296 B2
(45) Date of Patent: Nov. 20, 2018

(54) APPARATUS AND METHOD FOR NONINVASIVELY MEASURING BIO-ANALYTE AND APPARATUS AND METHOD FOR DIAGNOSING METABOLIC SYNDROME

(71) Applicant: SAMSUNG ELECTRONICS CO., LTD., Suwon-si (KR)

(72) Inventors: Joonhyung Lee, Yongin-si (KR);
Sangkyu Kim, Yongin-si (KR);
Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 572 days.

(21) Appl. No.: 14/810,710

(22) Filed: Jul. 28, 2015

(65) Prior Publication Data
US 2016/0051180 A1    Feb. 25, 2016

(30) Foreign Application Priority Data
Aug. 25, 2014    (KR) .................. 10-2014-0110959

(51) Int. Cl.
*A61B 5/1455*    (2006.01)
*A61B 5/00*    (2006.01)
*A61B 5/145*    (2006.01)

(52) U.S. Cl.
CPC ............ *A61B 5/443* (2013.01); *A61B 5/0075* (2013.01); *A61B 5/1455* (2013.01); *A61B 5/14546* (2013.01); *A61B 5/7278* (2013.01); *A61B 5/7282* (2013.01)

(58) Field of Classification Search
CPC .... A61B 5/1455; A61B 5/7578; A61B 5/7282
See application file for complete search history.

(56) References Cited

U.S. PATENT DOCUMENTS

| | | | |
|---|---|---|---|
| 8,137,922 B2 | 3/2012 | Dieplinger et al. | |
| 8,355,767 B2* | 1/2013 | Hunter | A61B 5/14532 600/316 |
| 8,357,500 B2 | 1/2013 | Younossi et al. | |
| 2002/0016534 A1 | 2/2002 | Trepagnier et al. | |
| 2011/0251659 A1 | 10/2011 | Prescott | |
| 2012/0328594 A1* | 12/2012 | McKenna | G01N 33/66 424/94.4 |
| 2013/0210041 A1 | 8/2013 | Anderberg et al. | |

FOREIGN PATENT DOCUMENTS

WO    2014/049131 A1    4/2014

OTHER PUBLICATIONS

Communication dated Jan. 26, 2016, issued by the European Patent Office in counterpart European Application No. 15181454.8.
Annika M. K. Enejder et al: "Raman spectroscopy for noninvasive glucose measurements", Journal of Biomedical Optics, vol. 10, No. 3, Jan. 1, 2005 (Jan. 1, 2005), p. 031114-1-031114-9, XP055018261, ISSN: 1083-3668, DOI: 10.1117/1.1920212.

* cited by examiner

*Primary Examiner* — Eric Winakur
(74) *Attorney, Agent, or Firm* — Sughrue Mion, PLLC

(57) ABSTRACT

An apparatus for noninvasively measuring a bio-analyte including a metering device configured to obtain at least one of light and electrical information representative of an amount of fibrous protein from skin of a subject; and a processor configured to determine information representative of an amount an analyte present in blood of the subject based on the obtained information representative of an amount of the fibrous protein.

21 Claims, 11 Drawing Sheets

APPARATUS AND METHOD FOR NONINVASIVELY MEASURING BIO-ANALYTE AND APPARATUS AND METHOD FOR DIAGNOSING METABOLIC SYNDROME

RELATED APPLICATION

This application claims priority from Korean Patent Application No. 10-2014-0110959, filed on Aug. 25, 2014 in the Korean Intellectual Property Office, the disclosure of which is incorporated herein in its entirety by reference.

BACKGROUND

1. Field

Apparatuses and methods consistent with exemplary embodiments relate to noninvasively measuring of a bio-analyte or diagnosing a metabolic syndrome.

2. Description of the Related Art

As medical science has progressed and an average life expectancy has increased, interest in health care has also increased. Accordingly, the interest in medical devices has also increased. Interest has particularly grown in small-sized and medium-sized medical devices that are used in public places, and small medical devices and health care devices that can be carried by individuals. Various medical devices that are used in hospitals or health examination centers have also increased.

An invasive measuring method is often used during medical examination. Such invasive methods may include extracting blood of a subject and measuring and analyzing the blood. The invasive measuring method has disadvantages. For example, the subject feels pain when the blood is extracted. In addition, reagents that react with the specific material of the blood have to be used when the blood is analyzed, and colorimetric assays and optical equipment have to be used. These result in an uncomfortable and cumbersome analysis.

SUMMARY

One or more exemplary embodiments provide apparatuses and methods for noninvasively measuring a bio-analyte.

One or more exemplary embodiments also provide Provided are apparatuses and methods for diagnosing a metabolic syndrome.

One or more exemplary embodiments also provide measuring (diagnosis) apparatuses and measuring (diagnosis) methods that may measure a target analyte in blood without extracting the blood.

One or more exemplary embodiments also provide Provided are apparatuses and methods for noninvasively measuring a bio-analyte (apparatuses and methods for diagnosing metabolic syndrome) that detect or analyze a first material in a first body part of a subject and output information about a second material in a second body part of the subject.

According to an aspect of an exemplary embodiment, there is provided an apparatus for noninvasively measuring a bio-analyte, the apparatus including a metering device configured to obtain raw data comprising the information representative of fibrous protein from skin of a subject and a processor configured to determine information representative of an amount of an analyte present in blood of the subject based on the obtained information representative of an amount of fibrous protein.

The metering device is configured to out a measurable characteristic to obtain an amount of collagen in the skin of the subject.

The metering device is configured to output a measurable characteristic to obtain an amount of type I collagen in the skin of the subject.

The processor is configured to relate the obtained information representative of the amount of the fibrous protein to the amount of analyte to provide an index of a metabolic syndrome.

The processor is configured to relate the obtained information representative of the amount of the fibrous protein to an amount of adiponectin.

The metering device may include a Raman spectrometer.

The processor may be configured to process data by using a correlation between the fibrous protein and the analyte.

The metering device may comprise a Raman spectrometer configured to obtain the raw data comprising the information representative of an amount of the fibrous protein from the skin of the subject by using the Raman spectrometer.

The metering device may be configured to obtain Raman spectrum data of the skin of the subject and read an intensity value corresponding to at least one wavenumber of a wavenumber range of about 853~857 $cm^{-1}$, 934~938 $cm^{-1}$, 1447~1452 $cm^{-1}$, and 1656~1660 $cm^{-1}$ from the Raman spectrum data to obtain the information about the fibrous protein.

According to an aspect of another exemplary embodiment, there is provided an apparatus for diagnosing a metabolic syndrome, the apparatus including a metering device configured to obtain information representative of an amount of a first material relating to skin tissue of a subject and a processor configured to determine information regarding a second material relating to the metabolic syndrome in blood of the subject, based on the information regarding the first material.

The metering device is configured to output a measurable characteristic to determine an amount of collagen in the skin of the subject.

The metering device is configured to output a measurable characteristic to obtain an amount of type I collagen in the skin of the subject.

The processor is configured to relate the obtained information representative of the amount of the first tissue in the skin to an amount of adiponectin.

The apparatus may include a metering device including a Raman spectrometer configured to obtain raw data including the information representative of the amount of the first material from the skin of the subject.

According to an aspect of another exemplary embodiment, there is provided a method of diagnosing a metabolic syndrome, the method including obtaining information regarding fibrous protein from skin of a subject; and determining information regarding a material relating to the metabolic syndrome in blood of the subject based on the information regarding the fibrous protein.

The fibrous protein may include collagen.

The collagen may include type I collagen.

The material relating to the metabolic syndrome may include adiponectin.

The obtaining the information regarding fibrous protein may include: performing Raman spectroscopic analysis on the skin of the subject The method may further include: determining a correlation between the fibrous material and the material relating to the metabolic syndrome, wherein the determining the information regarding the material relating to the metabolic syndrome includes: using an algorithm based on the correlation.

The method may be non-invasively performed.

BRIEF DESCRIPTION OF THE DRAWINGS

The above and/or other aspects will become apparent and more readily appreciated from the following description of exemplary embodiments, taken in conjunction with the accompanying drawings in which.

DETAILED DESCRIPTION

Figure 1:
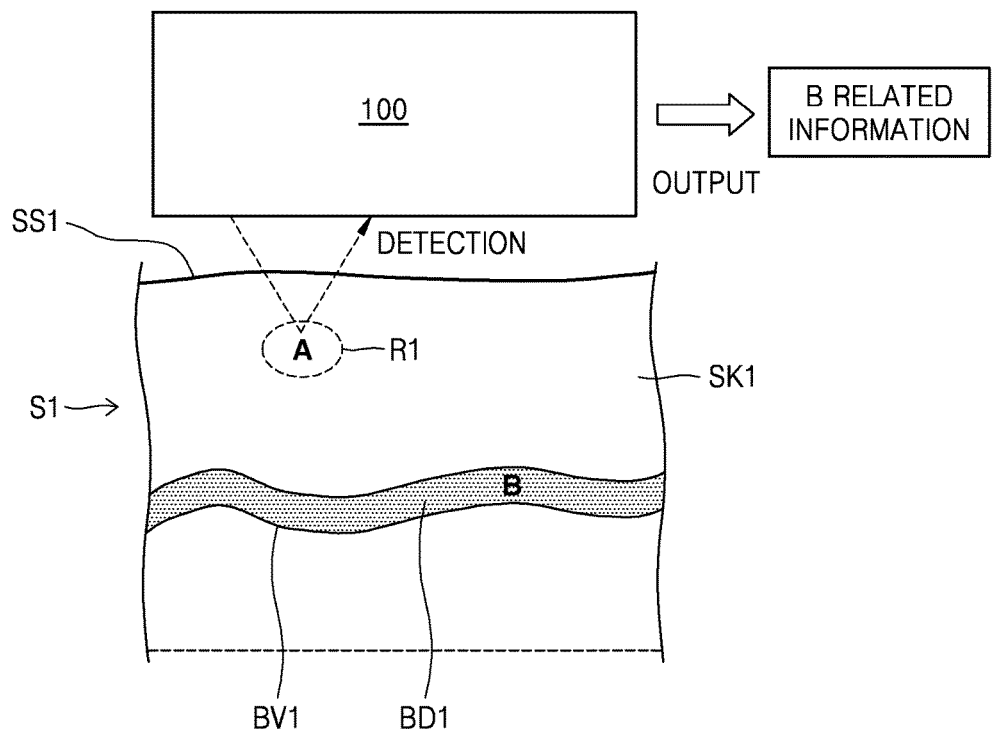
FIG. 1 is a conceptual view for explaining an apparatus for noninvasively measuring a bio-analyte according to an exemplary embodiment.

Various exemplary embodiments will now be described more fully with reference to the accompanying drawings in which exemplary embodiments are shown.

It will be understood that as used herein the term "and/or" includes any and all combinations of one or more of the associated listed items.

It will be understood that, although the terms "first", "second", etc. may be used herein to describe various elements, components, regions, layers and/or sections, these elements, components, regions, layers and/or sections should not be limited by these terms. These terms are only used to identify one element, component, region, layer, or section from another element, component, region, layer, or section. Thus, a first element, component, region, layer, or section discussed below could be termed a second element, component, region, layer, or section without departing from the teachings of exemplary embodiments.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" may encompass a relative location with a different apparatus orientation. The device may be otherwise oriented (rotated 90 degrees or at other orientations) and the spatially relative descriptors used herein interpreted accordingly.

The terminology used herein is for the purpose of describing particular embodiments only and is not intended to be limiting of exemplary embodiments. As used herein, the singular forms "a," "an", and "the" are intended to include the plural forms as well, unless the context clearly indicates otherwise.

Exemplary embodiments are described herein with reference to cross-sectional illustrations that are schematic illustrations and/or intermediate structures of exemplary embodiments. As such, variations from the illustrated shapes are to be expected due to manufacturing techniques and/or tolerances. Thus, exemplary embodiments should not be construed as limited to the particular shapes of regions illustrated herein but are to include deviations in shapes that result, for example, from manufacturing. For example, an implanted region illustrated as a rectangle will typically have rounded or curved features and/or a gradient of implant concentration at its edges rather than a binary change from an implanted to a non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of exemplary embodiments.

Unless otherwise defined, all terms (including technical and scientific terms) used herein have the same meaning as commonly understood by one of ordinary skill in the art to which exemplary embodiments belong. Exemplary embodiments will now be described more fully with reference to the accompanying drawings, in which exemplary embodiments are shown. Widths and thicknesses of layers or regions in the appended drawings are exaggerated for clarity. The same reference numerals denote the same elements throughout. Expressions such as "at least one of," when preceding a list of elements, modify the entire list of elements and do not modify the individual elements of the list.

FIG. 1 is a conceptual view for explaining an apparatus for noninvasively measuring a bio-analyte 100 according to an exemplary embodiment. Hereinafter, a noninvasive living body measurement apparatus 100 may be referred to as a non-invasive measuring device. The term bio-analyte may include a constituent material of a body of a living creature or animal such as a human or a component of the constituent material. The bio-analyte may refer to a constituent material of a subject S1 to be measured by the noninvasive measuring apparatus 100. For example, the bio-analyte may be a material that is included in tissue or blood of the subject S1 or a component of the material. A first material A and a second material B which will be explained below may be included in the bio-analyte. Also, the subject S1 itself may be considered to be the bio-analyte. The term bio-analyte may encompass a general target analyte that is used in medical fields or diagnosis and/or measurement fields.

Referring to FIG. 1, the noninvasive measuring apparatus 100 may be an apparatus for noninvasively measuring the subject S1. The noninvasive measuring apparatus 100 may be an apparatus that obtains information about the first material A from a first body part of the subject S1 and outputs information about the second material B that exists in a second body part of the subject S1 based on the information about the first material A. In other words, the noninvasive measuring apparatus 100 may be configured to obtain the information about the first material A in the first body part by detecting and measuring the first body part and to output the information about the second material B of the second body part based on the information about the first material A.

The first body part and the second body part of the subject S1 may differ. For example, the first body part may be skin SK1 (i.e., tissue) of the subject S1, and the second body part may be blood BD1 present in a blood vessel BV1 of the subject S1. The first body part may exist at a first depth from a surface (detected surface) SS1 of the subject S1, and the second body part may exist at a second depth which is greater than the first depth, from the surface SS1. Accordingly, the second body part may be farther than the first body part from the noninvasive measuring apparatus 100. A reference numeral R1 is a region where measurement is performed by the noninvasive measuring apparatus 100, i.e. a measurement region. The first body part is the skin SK1, and the second body part is blood BD1 in this regard. However, according to circumstances, the first body part may be tissue of a body part (for example, an organ) other than the skin SK1 and the second body part may not be the blood BD1, but another body element.

The first body part, for example, the first material A present in the skin SK1, and the second body part, for example, the second material B present in the blood BD1, may differ. The first material A may be fibrous protein. The fibrous protein may be scleroprotein. For example, the first material A may be collagen, and the collagen may be a type I collagen. The type I collagen will be described in detail below, with reference to FIG. 8. The second material B may be related to a metabolic syndrome. For example, the second material B may be adiponectin. Adiponectin and a relationship between adiponectin and metabolic syndrome will be described in detail below, with reference to FIG. 9.

There may be a correlation between the information about the first material A in the skin SK1 and the information about the second material B in the blood BD1. The noninvasive measuring apparatus 100 may be configured to determine the information about the second material B from the information about the first material A according to an algorithm or observation, based on the correlation. In other words, the information about the first material may be acquired from the skin SK1 of the subject S1, and the information about the second material B in the blood BD1 may be derived based on the information about the first material and the correlation. Thus, the information about the second material B in the blood BD1 may be obtained without having to extract the blood BD1 or directly detect the blood BD1. The correlation and the information determination (data processing) using the correlation will be explained below in detail.

As described above, the second material B is related to a metabolic syndrome, and thus the noninvasive measuring apparatus 100 may be used to diagnose a metabolic syndrome. Thus, the noninvasive measuring apparatus 100 may be referred to as a metabolic syndrome diagnosis apparatus. However, if a type of the second material B is different, a purpose of the noninvasive measuring apparatus 100 may also be different.

Figure 2:
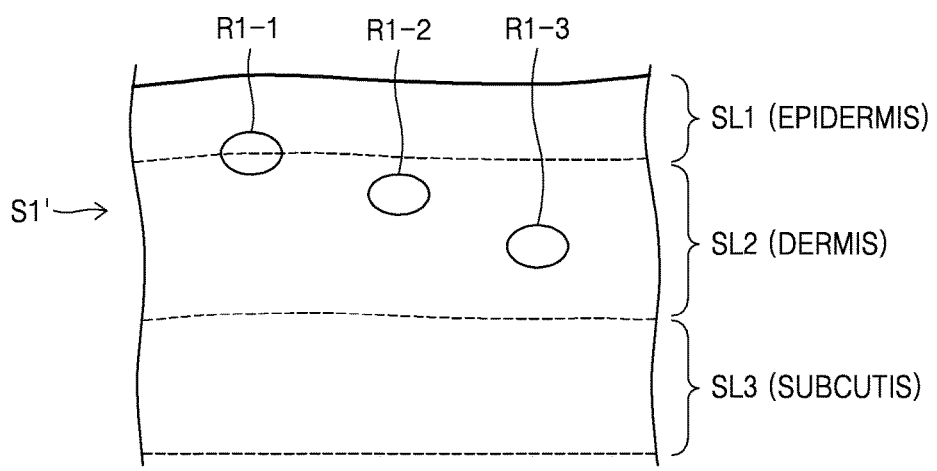
FIG. 2 is a cross-sectional view for explaining a body part of a subject that is measured by using the noninvasive measuring apparatus of FIG. 1, according to an exemplary embodiment.

FIG. 2 is a cross-sectional view for explaining a measured region (body part) of a subject S1' that is measured by using the noninvasive measuring apparatus 100 of FIG. 1, according to an exemplary embodiment.

Referring to FIG. 2, the skin of the subject S1' may include an epidermis SL1 and a dermis SL2. The epidermis SL1 exists on an outer portion of the skin and the dermis SL2 exists under the epidermis SL1. A subcutis SL3 may exist under the dermis SL2. A blood vessel (not shown) may exist in the subcutis SL3, and a blood vessel (not shown) or a capillary may also exist in the dermis SL2. When the subject S1' is measured by using the noninvasive measuring apparatus 100 (see FIG. 1) according to an exemplary embodiment, the subject S1' may be (directly) measured through the dermis SL2 mainly or a region including the epidermis SL1 and the dermis SL2. First through third measured regions R1-1, R1-2, and R1-3 of FIG. 2 are various measured body parts having different depths. The first through third measured regions R1-1, R1-2, and R1-3 may correspond to the first body part R1 of FIG. 1. In other words, the first through third measured regions R1-1, R1-2, and R1-3 may be regions that are directly measured and/or detected by the noninvasive measuring apparatus 100 (see FIG. 1). A region including a part of the epidermis SL1 and a part of the dermis SL2 such as the first measured region R1-1 may be measured, or a region of the dermis SL2 such as the second and third measured regions R1-2 and R1-3 may be measured. The first material A described with reference to FIG. 1 may be fibrous protein, for example, collagen. Because collagen may be mainly present in the dermis SL2, the noninvasive measuring apparatus 100 (see FIG. 1) may be used to measure the region of the dermis SL2 mainly or the region including the epidermis SL1 and the dermis SL2.

A depth and/or range of a measured body part (e.g., the first body part R1 of FIG. 1) may vary according to a measurement method and/or a measurement unit that is used by the noninvasive measuring apparatus 100 of FIG. 1. An exemplary noninvasive measuring apparatus 100 (see FIG. 1) performs measurements by using the Raman spectrometer. Because the Raman spectrometer uses a laser source, a depth/range of the measured region (R1 of FIG. 1) may vary according to a wavelength of a laser generated by the laser source. When the Raman spectrometer is used, not only the region of the epidermis SL1 but also the region of the dermis SL2 may be measured.

Figure 3:
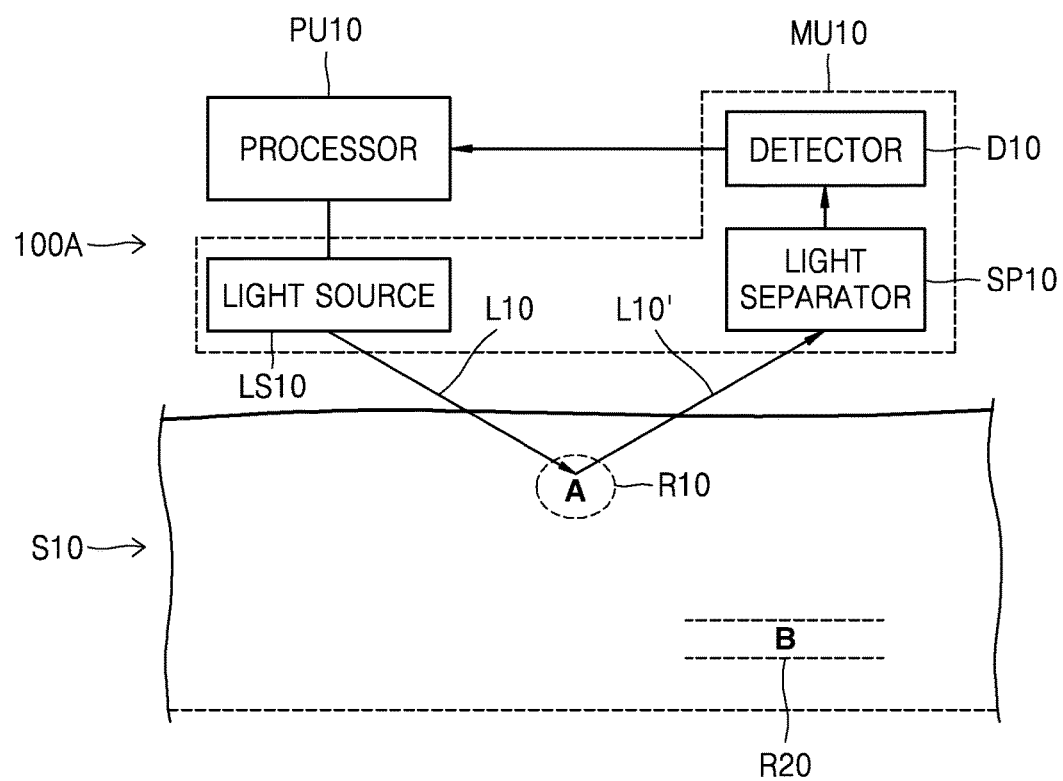
FIG. 3 is a block diagram for explaining a configuration of a noninvasive measuring apparatus, according to an exemplary embodiment.

FIG. 3 is a block diagram for explaining a configuration of a noninvasive measuring apparatus 100A, according to an exemplary embodiment.

Referring to FIG. 3, the noninvasive measuring apparatus 100A may include a measurer or metering device MU10 that obtains raw data including information about the first material A from a first region R10 of a subject S10. The measurer MU10 may also be referred to as a data obtainer. Also, the noninvasive measuring apparatus 100A may include a processor PU10. The processor PU10 may include a data processor that determines or derives information about the second material B in a second region R20 of the subject S10 based on the information about the first material A. The processor PU10 may determine or derive the information about the second material B from the information about the first material A by using the data processor. In this case, an algorithm based on a correlation between the first material A and the second material B may be used. The first region R10 may correspond to the measured region R1 of FIG. 1, and the measured regions R1-1, R1-2, and R1-3 of FIG. 2, and the second region R20 may correspond to the second body part described with reference to FIG. 1. The first region R10 may the skin or the tissue, and the second region R20 may be blood in a blood vessel. The regions R10 and R20 may correspond to analogous regions described above in FIGS. 1 and 2.

The measurer MU10 may measure the first region R10 by using light. In this case, the measurer MU10 may include a light source LS10 that emits light L10 to the first region R10 and a detector D10 that detects light L10' that is emitted from the light source LS10 and is reflected or scattered by the first region R10. The measurer MU10 may further include a light separator SP10 that separates the light L10' that is reflected or scattered by the first region R10. The light that is separated by the light separator SP10 may be detected by the detector D10. The light separator may include a filter or other optical device. Raw data about the first region R10 may be obtained by using the measurer MU10. The raw data may include the information about the first material A.

The raw data that is obtained by the measurer MU10 may be transmitted to the processor PU10. The processor PU10 may extract the information about the first material A from the raw data, and may determine or derive the information about the second material B in the second region R20 based on the extracted information about the first material A. The extraction and the determination of the information (data) may be performed by the data processor. Also, the processor PU10 may function to control an overall operation of the noninvasive measuring apparatus 100A including the measurer MU10 as well as extract or determine the data. To this end, the processor PU10 may further include a controller and may be connected to the light source LS10 and the detector D10.

Although not shown in FIG. 3, the noninvasive measuring apparatus 100A may further include an output device that is connected to the processor PU10. The output device may include, for example, a display device. The information about the second material B that is derived by the processor PU10 may be output through the output device. When the second material B is related to a metabolic syndrome, content relating to a metabolic syndrome may be output through the output device. The output device will be explained below in detail with reference to FIG. 7.

Figure 4:
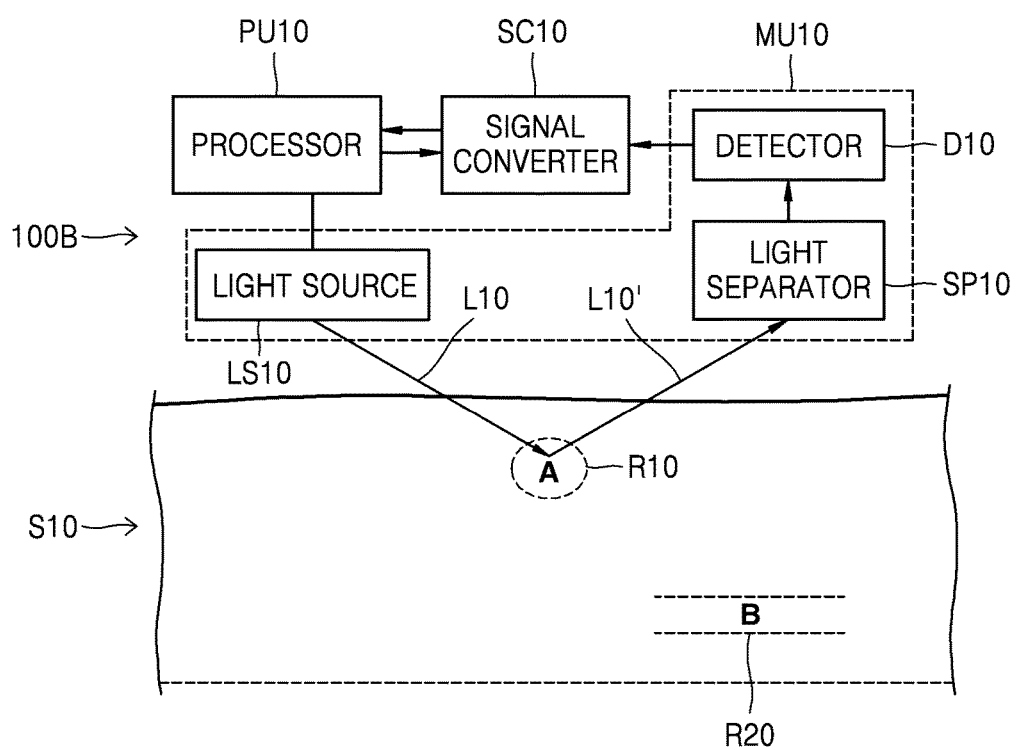
FIG. 4 is a block diagram for explaining a configuration of a noninvasive measuring apparatus, according to another exemplary embodiment.

According to another embodiment, a signal converter may be further provided between the measurer MU10 (data obtainer) and the processor PU10 (data processor) of FIG. 3. That is, as shown in FIG. 4, a noninvasive measuring apparatus 100B may further include a signal converter SC10 that is disposed between the measurer MU10 (signal obtainer) and the processor PU10 (data processor). The signal converter SC10 may include, for example, an analog front-end (AFE) circuit. The signal converter SC10 may convert an analog signal that is input from the measurer MU10 (data obtainer) into a digital signal and may transmit the digital signal to the processor PU10 (data processor). The processor PU10 may transmit a control signal to the signal converter SC10. The signal converter SC10 may operate according to the control signal of the processor PU10. Accordingly, signal transmission (that is, communication) may occur between the processor PU10 and the signal converter SC10.

Figure 5:
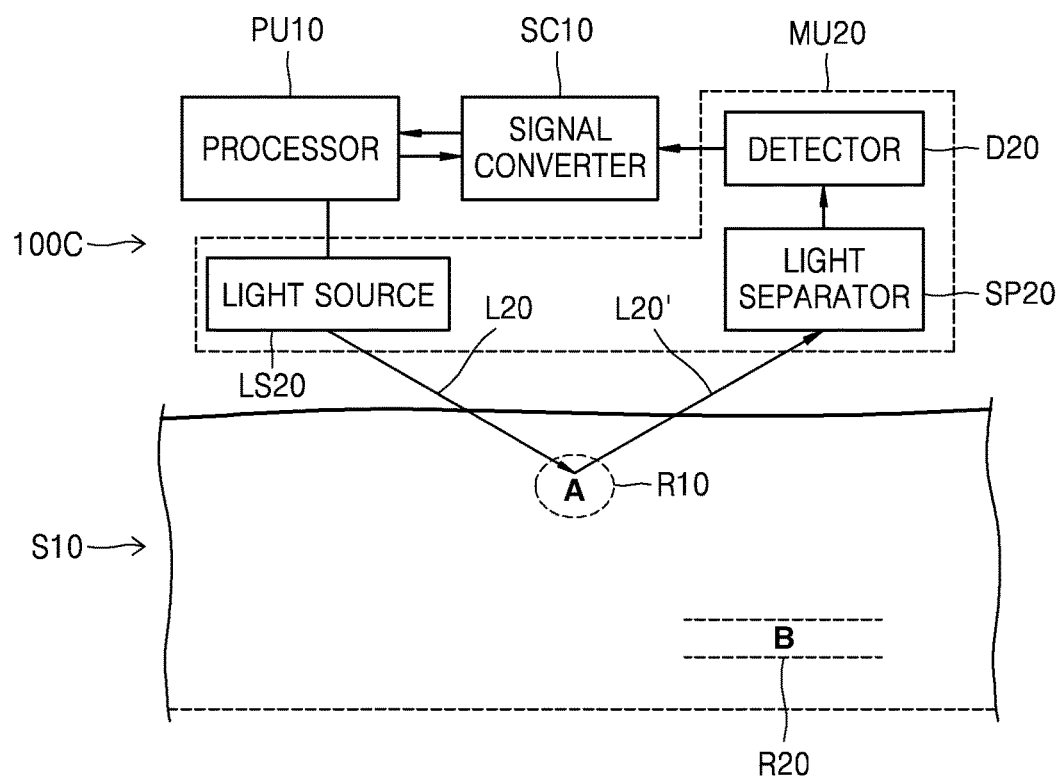
FIG. 5 is a block diagram for explaining a configuration of a noninvasive measuring apparatus, according to another exemplary embodiment.

A Raman spectrometer may be used for the measurer MU10 of FIG. 3 or 4, as is shown in FIG. 5.

Referring to FIG. 5, a measurer or metering device MU20 of a noninvasive measuring apparatus 100C may include a laser source LS20 as a light source. Light L20 may be emitted by the laser source LS20 to the first region R10 of the subject S10. The light L20 may be a laser. Light L20' that is scattered by the first region R10 may be separated by a light separator SP20 and may be detected by a detector D20. The measurer MU20, including the laser source LS20, the light separator SP20, and the detector D20, may be a Raman spectrometer. Information about the first material A in the first region R10 may be obtained by measuring the first region R10 by using the measurer MU20, and information about the second material B in the second region R20 may be determined and derived based on the information about the first material A by using the processor PU10. The signal converter SC10 may be further provided between the processor PU10 and the detector D20. Functions of the processor PU10 and the signal converter SC10 may be similar to those described with reference to FIGS. 3 and 4.

As shown in FIG. 5, when the Raman spectrometer is used for the measurer MU20, various advantages and effects may be obtained. When light (i.e. L20) of a single wavelength is scattered through interaction with a molecular vibration of a material, the Raman spectrometer uses a phenomenon in which energy of the light is shifted. A difference in an energy state between an incident light (i.e. L20) and a scattered light (i.e. L20'), e.g. an energy shift, may include information (a molecular structure and a combination shape) relating to the molecular vibration of the material, and provide information (e.g. a fingerprint) regarding a functional group. Thus, a precise molecular identification may be possible through a Raman spectrum analysis. In particular, when a target material to be detected (e.g. the first material A) is fibrous protein such as collagen, the Raman spectrometer may be advantageous to an analysis of the target material. When the Raman spectrometer is used, since a measurement depth (penetration depth of light) may be easily controlled, an epidermis region of the subject S10 and a dermis region may be easily analyzed.

The first material A of FIGS. 3 through 5 may be fibrous protein present in the skin or the tissue. The fibrous protein may be scleroprotein. For example, the first material A may be collagen. The collagen may be type I collagen. The second material B is present in the blood, and may be related to a metabolic syndrome. For example, the second material B may be adiponectin. Information regarding the first material A and information regarding the second material B may have a correlation. The noninvasive measuring apparatuses 100A through 100C may derive or determine the information regarding the second material B based on the information regarding the first material A. As a result, information regarding a metabolic syndrome may be output. Thus, the noninvasive measuring apparatuses 100A through 100C may be a metabolic syndrome diagnosis apparatuses.

The detailed constructions of the measurers MU10 and MU20 of the noninvasive measuring apparatuses 100A through 100C described with reference to FIGS. 3 through 5 above are examples and may be modified in various ways. For example, locations of the light separators SP10 and SP20 may be different. According to circumstances, the light separators SP10 and SP20 may not be used. The light separators SP10 and SP20 and the detectors D10 and D20 may be integrated.

Meanwhile, the processor PU10 used in the noninvasive measuring apparatuses 100A through 100C described with reference to FIGS. 3 through 5 above may have the configuration shown in, for example, FIG. 6.

Figure 6:
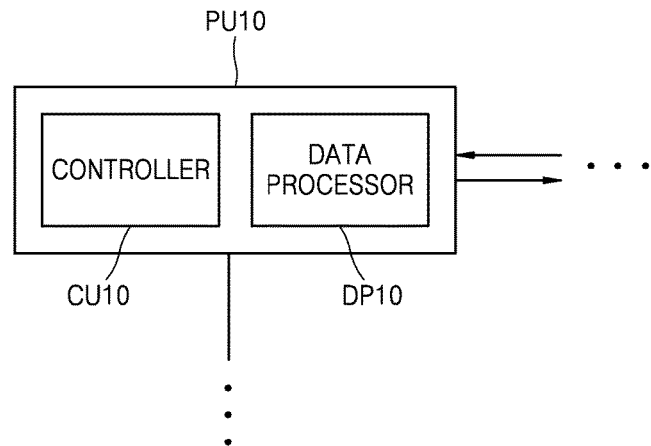
FIG. 6 is a block diagram for explaining a configuration of a processor that may be used in a noninvasive measuring apparatus, according to an exemplary embodiment.

Referring to FIG. 6, the processor PU10 may include a data processor DP10 and a controller CU10. The data processor DP10 may function to extract information about the first material A from raw data that is obtained by, for example, the measurer MU10 (see FIG. 3) and to determine or derive information about the second material B based on the extracted information about the first material A. The data processor DP10 may perform data processing by using an algorithm based on a correlation between the first material A and the second material B. The controller CU10 may function to control an overall operation of any of the noninvasive measuring apparatuses 100A through 100C including the measurer MU10. The processor PU10 may include a configuration or function of a central processing unit (CPU). Alternatively, the processor PU10 may include a configuration or function of a microcontroller unit (MCU).

Figure 7:
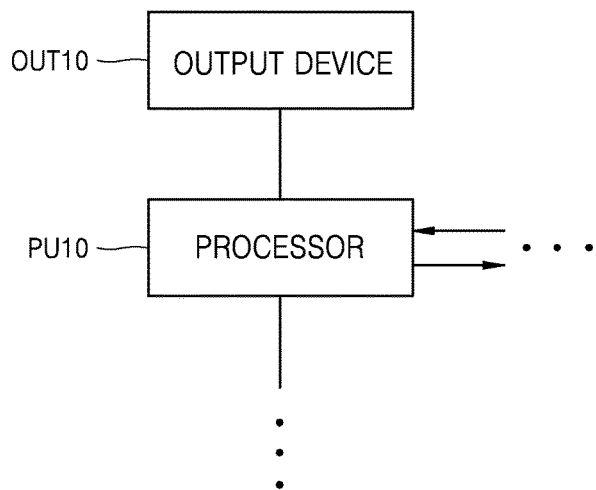
FIG. 7 is a block diagram for explaining a processor and an output device that may be used in a noninvasive measuring apparatus, according to an exemplary embodiment.

The noninvasive measuring apparatuses 100A through 100C described with reference to FIGS. 3 through 5 may further include an output device that is connected to the processor PU10, as shown in FIG. 7.

Referring to FIG. 7, an output device OUT10 that is connected to the processor PU10 may be further provided. The output device OUT10 may include, for example, a display device. The output device OUT10 may be directly connected to the processor PU10, and if necessary, the output device OUT10 and the processor PU10 may be connected to each other through wireless communication. A connection relationship between the output device OUT10 and the processor PU10 and a configuration of the output device OUT10 may be modified in various ways.

Figure 8:
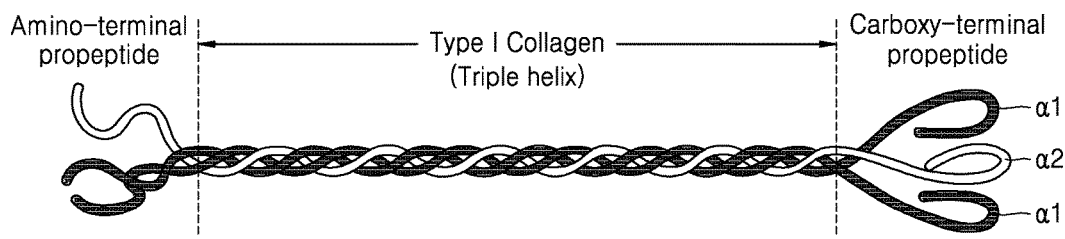
FIG. 8 is a diagram of a structure of type I collagen.

FIG. 8 is a diagram of a structure of type I collagen.

Referring to FIG. 8, the type I collagen may have a trimer structure in which three protein chains are twisted. In other words, the type I collagen may have a triple helix structure in which three polypeptide chains are twisted to form a helical structure. Two of the three polypeptide chains may be alpha 1 chains α1, and the other one may be an alpha 2 chain α2. The two alpha 1 chains α1 may have the same aminoacid sequence, and the alpha 2 chain α2 may have a different sequence. Carboxy-terminal propeptide may be present in one end of the type I collagen. Amino-terminal propeptide may be present in another end of the type I collagen. The whole structure of FIG. 8 may be the type I collagen.

Adiponectin is a type of protein generated or secreted in a fat cell, a marrow, a muscle cell, a heart muscle cell, and other cells and is known to be related to glucose regulation, fatty acid breakdown, and other body processes. A concentration of adiponectin may have a high correlation with factors that cause a metabolic syndrome.

The metabolic syndrome is a chronic metabolic disorder diagnosed by a co-occurrence of various diseases such as hyperlipidemia, elevated blood pressure, diabetes (or impaired glucose tolerance), obesity, cardiovascular arteriosclerosis, etc. These diseases are closely related to each other, and are related to an insulin resistance. The lower the concentration of the adiponectin, the greater the numerical value or index of the factors that cause a metabolic syndrome. In other words, the lower the concentration of the adiponectin, the greater the index or risk of the metabolic syndrome.

A body mass index (BMI) may have a negative correlation with a blood concentration of adiponectin. The negative correlation may be clearer in visceral fat than in subcutaneous fat. In connection with diabetes, adiponectin may act to increase an insulin sensitivity and reduce an insulin resistance. Thus, low adiponectin level has a high possibility of an index of diabetes. In connection with elevated blood pressure, a blood concentration of adiponectin may have a meaningful negative correlation with systolic/diastolic/average blood pressure. A low blood concentration of adiponectin is measured from an elevated blood pressure patient. In connection with hyperlipidemia, a blood concentration of adiponectin may have a negative correlation with a blood neutral fat concentration and an apolipoprotein concentration and have a positive correlation with a high-density lipoprotein (HDL) cholesterol concentration. In connection with a cardiovascular disease, the lower the concentration of adiponectin, the greater the factors that cause the cardiovascular disease. The low adiponectin level is regarded as a risk factor of atherosclerosis.

Figure 9:
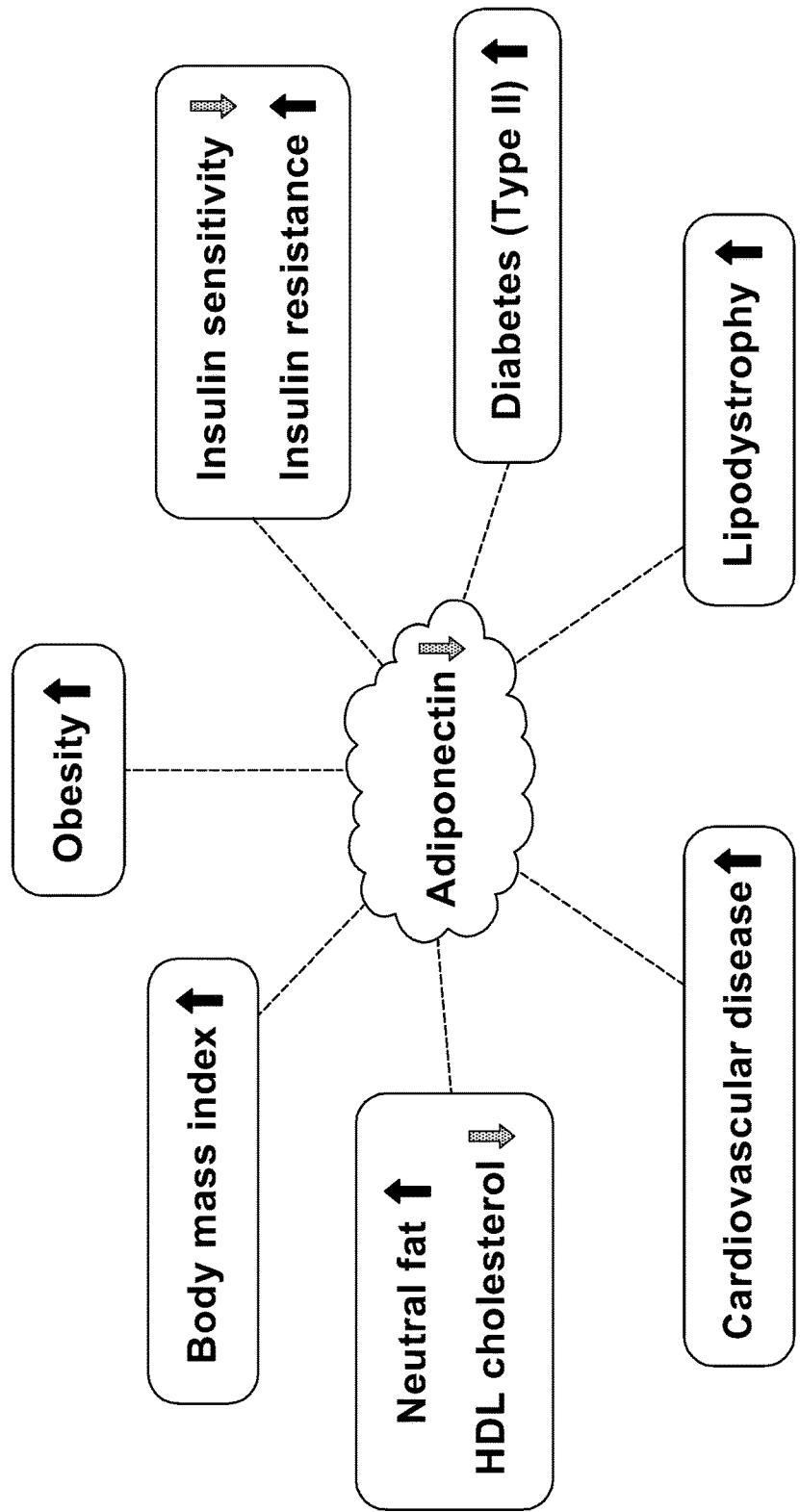
FIG. 9 is a diagram for explaining correlations between a blood concentration of adiponectin and metabolic syndrome factors.

FIG. 9 is a diagram for explaining correlations between a blood concentration of adiponectin and a metabolic syndrome factors.

Referring to FIG. 9, the lower the concentration of adiponectin, the lower the insulin sensitivity, and the greater the insulin resistance. In this connection, the lower the concentration of adiponectin, the greater the possibility of index of diabetes (type II diabetes). The lower the concentration of adiponectin, the greater the BMI, and the greater index of obesity. The lower the concentration of adiponectin, the greater the concentration of the neutral fat, and the lower the concentration of HDL cholesterol. The lower the concentration of adiponectin, the greater the possibility of the cardiovascular disease, and the greater the possibility of lipodystrophy.

The blood concentration of adiponectin has a negative correlation with skin fibrosis. If the skin fibrosis occurs, type I collagen may be abnormally generated in a dermis region of the skin. Thus, a concentration of type I collagen of the skin may have a meaningful correlation with the blood concentration of adiponectin. The higher the concentration of type I collagen of the skin, the lower the blood concentration of adiponectin. A low blood concentration of adiponectin may mean a high metabolic syndrome index or risk. Thus, information regarding type I collagen of the skin is detected or analyzed, and thus the blood concentration of adiponectin may be derived or determined and may be used to diagnose a metabolic syndrome.

Figure 10:
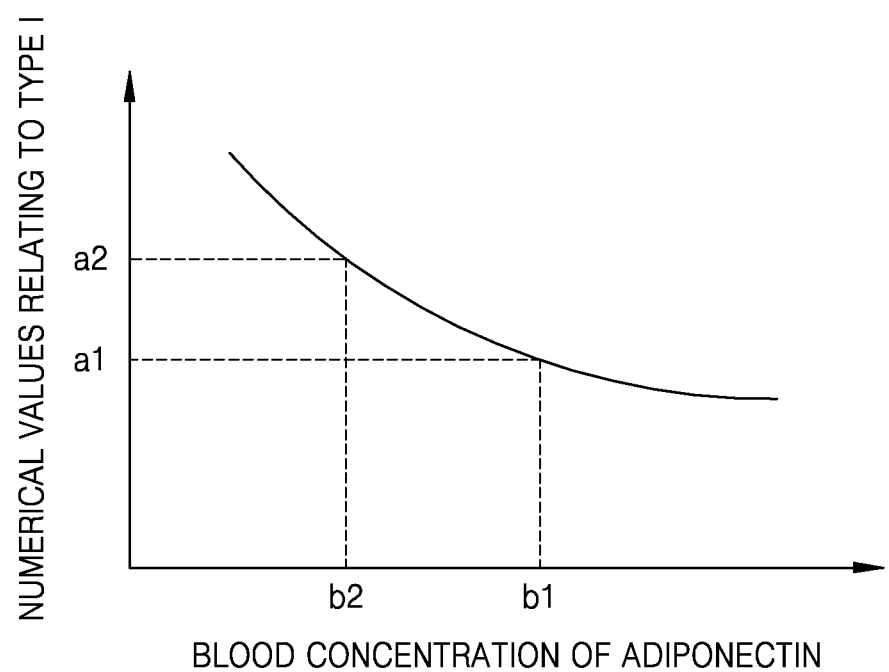
FIG. 10 is a graph of an example of a correlation between a numerical value of type I collagen detected by an apparatus for noninvasively measuring a bio-analyte and a blood concentration of adiponectin derived/determined by the apparatus for noninvasively measuring the bio-analyte according to an exemplary embodiment.

FIG. 10 is a graph of an example of a correlation between a numerical value of type I collagen detected by an apparatus for noninvasively measuring a bio-analyte and a blood concentration of adiponectin derived or determined by the apparatus for noninvasively measuring the bio-analyte according to an exemplary embodiment. Type I collagen may correspond to the first material A of FIG. 1. Adiponectin may correspond to the second material B of FIG. 1.

Referring to FIG. 10, the numerical value of type I collagen (hereinafter referred to as a collagen numerical value) obtained from skin or tissue of a subject and the blood concentration of adiponectin (hereinafter referred to as an adiponectin concentration) of the subject. The collagen numerical value and the adiponectin concentration may have a relationship described by a mathematical function, based on observation or prediction. The collagen numerical value and the adiponectin concentration may have an approximately inverse proportional relation or a similar relation. A measurer or metering device of the apparatus for noninvasively measuring the bio-analyte may be used to obtain raw data including information regarding collagen. A data processor of the apparatus for noninvasively measuring the bio-analyte may be used to extract the collagen numerical value from the raw data and derive the adiponectin concentration from the collagen numerical value. In this regard, the data processor may use the function relation (correlation). When the collagen numerical value is a1, the adiponectin concentration corresponding to the collagen numerical value a1 may be derived as b1 according to the function or correlation. When the collagen numerical value is a2, the adiponectin concentration corresponding to the collagen numerical value a2 may be derived as b2 according to the function or correlation. The value of a2 may be greater than a1. The value of b2 may be smaller than b1. A Metabolic syndrome index or risk of the subject may be determined based on the derived adiponectin concentration.

An example of a method of determining the correlation of FIG. 10 will be described below as an exemplary embodiment.

A plurality of samples (human samples) may be used to determine the correlation between type I collagen present in the tissue and adiponectin present in the blood. Data regarding type I collagen present in the tissue and data regarding adiponectin present in the blood may be obtained from the samples and then the correlation or equation between the two pieces of data may be obtained.

Figure 11:
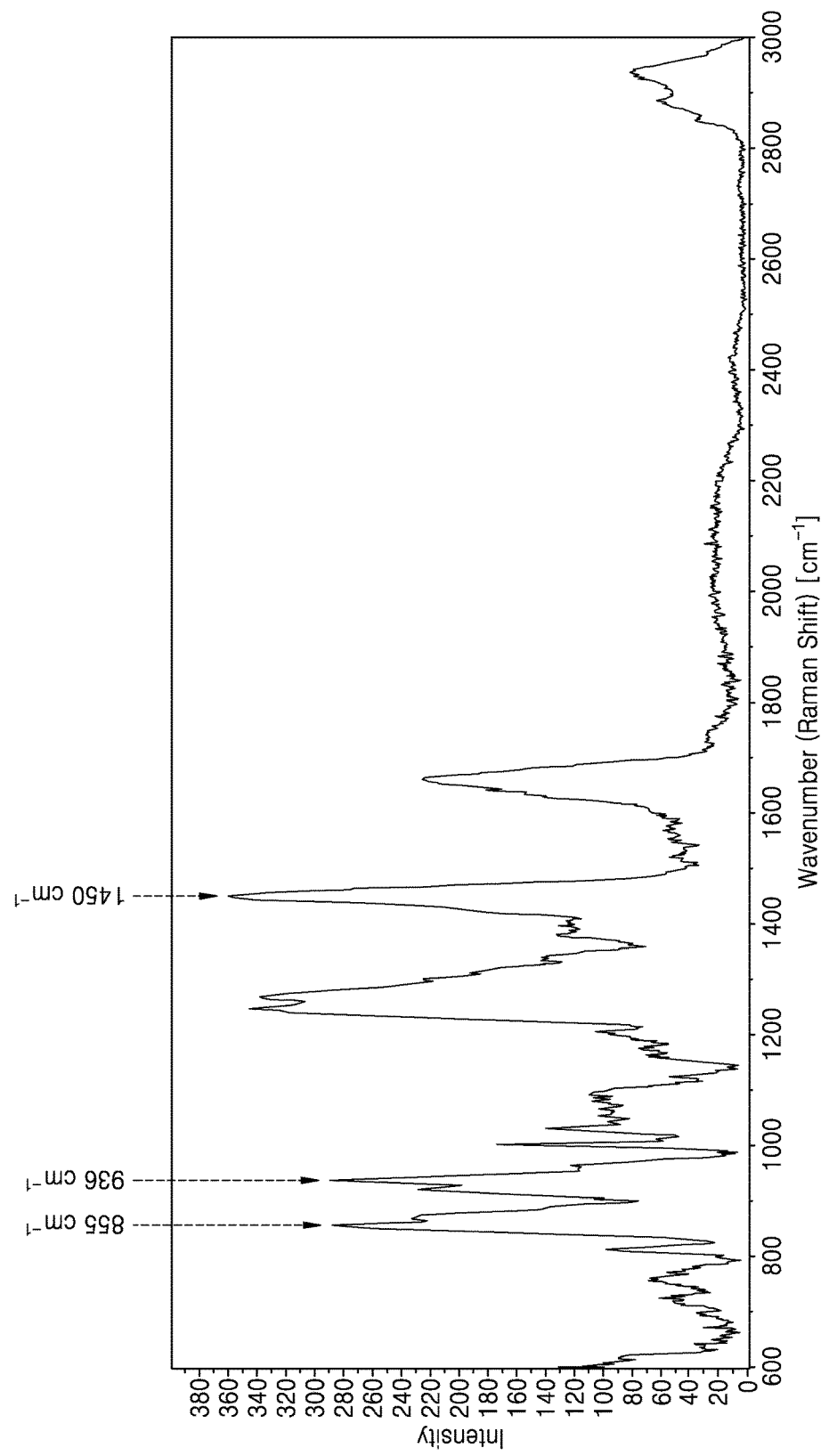
FIG. 11 is a graph of Raman spectrum data obtained from the skin tissue of one of a plurality of samples.

FIG. 11 is a graph of Raman spectrum data obtained from the skin tissue of one of a plurality of samples (human samples). The Raman spectrum data may be obtained by performing Raman spectroscopic analysis on the skin tissue (dermis tissue).

A method of extracting information regarding type I collagen from the Raman spectrum data of FIG. 11 will now be described. Wavenumbers relating to type I collagen included in the Raman spectrum data may include about 853~857 $cm^{-1}$, 934~938 $cm^{-1}$, 1447~1452 $cm^{-1}$, and 1656~1660 $cm^{-1}$. Thus, the information regarding type I collagen may be obtained by reading an intensity value corresponding to at least one of a wavenumber range of about 853~857 $cm^{-1}$, 934~938 $cm^{-1}$, 1447~1452 $cm^{-1}$, and 1656~1660 $cm^{-1}$ from the Raman spectrum data. For example, numerical values relating to type I collagen may be obtained by reading an intensity value corresponding to about 855 $cm^{-1}$, an intensity value corresponding to about 936 $cm^{-1}$, an intensity value corresponding to about 1450 $cm^{-1}$, an intensity value corresponding to 1658 $cm^{-1}$, etc. from the Raman spectrum data. The numerical values relating to type I collagen may be normalized by dividing the numerical values relating to type I collagen by an intensity value corresponding to a reference wavenumber. Such normalizing may offset a measurement deviation between the samples. The reference wavenumber for normalizing the numerical values may be modified in various ways. The same operation may be performed on all the samples.

A blood concentration of adiponectin of each sample may be measured by extracting blood from the same sample (human being). The blood concentration of adiponectin of each blood sample and the numerical values of type I collagen in the tissue of each sample obtained from the Raman spectrum data of FIG. 11 may be plotted. As a result, a graph of FIG. 12 may be obtained.

Figure 12:
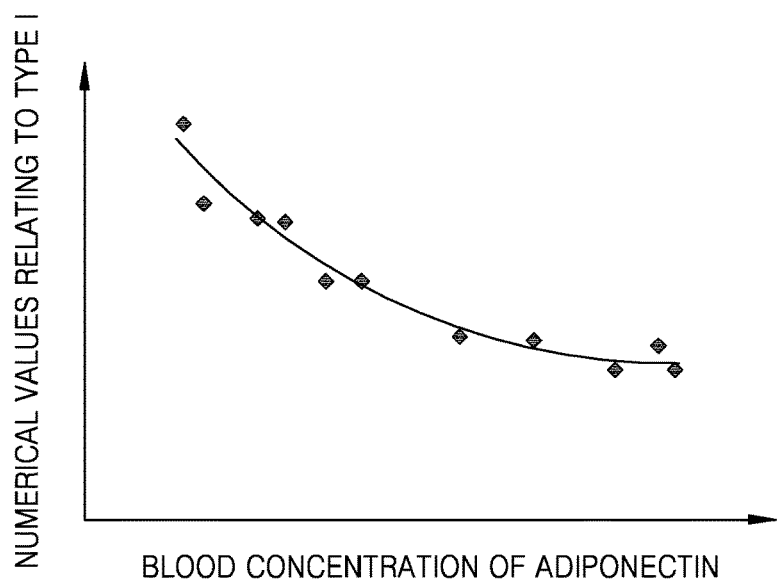
FIG. 12 is a graph of an example of a correlation between a numerical value of type I collagen of a subject and a blood concentration of adiponectin according to an exemplary embodiment.

Referring to FIG. 12, results corresponding to the samples may be a plurality of dots. In this regard, X axis values are the blood concentration of adiponectin, and Y axis values are the numerical values of type I collagen. The numerical values of type I collagen may be obtained by reading the intensity values of the wavenumbers relating to type I collagen from, for example, the Raman spectrum data of FIG. 11 and dividing the intensity values by the intensity value corresponding to the reference wavenumber. As an example, the numerical values of type I collagen may be determined as Intensity(855 $cm^{-1}$)/Intensity(811 $cm^{-1}$) or [Intensity(855 $cm^{-1}$)+Intensity(1450 $cm^{-1}$)]/Intensity(811 $cm^{-1}$). In this regard, 855 $cm^{-1}$ and 1450 $cm^{-1}$ are the wavenumbers relating to type I collagen, and 811 $cm^{-1}$ is the reference wavenumber.

A distribution of the dots of FIG. 12 has a clear tendency. That is, the numerical values of type I collagen and the blood concentration of adiponectin have a correlation. The correlation may be expressed as a function or mathematical equation. For example, the correlation may be expressed as a second order function (a secondary function graph). Higher order functionals, rational functions or other types of functions may also be used to express the relationship between the type I measurement and adiponectin measurement. The function may also be derived for different groups or patient studies. These may include categories of age, gender, and/or race.

A data processor of the apparatus for noninvasively measuring the bio-analyte according to an embodiment may include algorithm based on the correlation. Thus, if a numerical value of the first material A (e.g. collagen), i.e. the Y axis value, is obtained from the Raman spectrum data, a numerical value of the second material B (e.g. adiponectin), i.e., the X axis value, may be determined or derived from the correlation. For example, raw data including information regarding the first material A (e.g. collagen) may be obtained by using the measurer MU20 of FIG. 4, and information regarding the second material B (e.g. adiponectin) may be determined/derived from the raw data by using a data processor of the processor PU10.

The result of FIG. 12 is an example for convenience of description and may vary. Although the information regarding type I collagen is extracted by reading the intensity value corresponding to a specific wavenumber relating to type I collagen from the Raman spectrum data in FIGS. 11 and 12, the information regarding type I collagen in the tissue may be normalized by using intensity information of entire spectrum wavelengths and various regression analyses. A partial least square (PLS) may be used as an example of the regression analysis.

Figure 13:
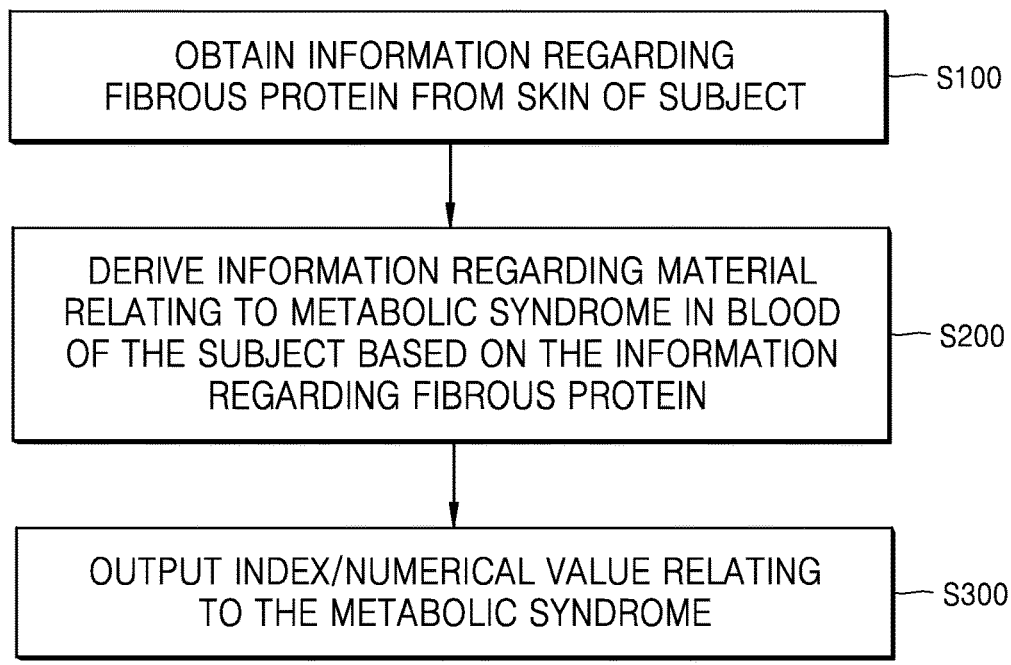
FIG. 13 is a flowchart for explaining a method of noninvasively measuring a bio-analyte according to an exemplary embodiment.

FIG. 13 is a flowchart for explaining a method of noninvasively measuring a bio-analyte according to an exemplary embodiment. The description of the apparatuses for noninvasively measuring the bio-analyte of 100A through 100C and related descriptions of FIGS. 1 through 12 may also be applied to FIG. 13. Accordingly, the method of noninvasively measuring the bio-analyte of FIG. 13 may be understood based on the description of FIGS. 1 through 12.

Referring to FIG. 13, the method of noninvasively measuring the bio-analyte (hereinafter referred to as the noninvasive measuring method) of an exemplary embodiment may include an operation (S100) of obtaining information regarding fibrous protein from the skin of a subject, an operation (S200) of determining information regarding a material relating to a metabolic syndrome in the blood of the subject based on the information regarding fibrous protein, and an operation (S300) of outputting an index or numerical value relating to the metabolic syndrome.

The fibrous protein may include collagen. The collagen may be type I collagen. The material relating to a metabolic syndrome may include adiponectin. The operation (S100) of obtaining the information regarding fibrous protein may include an operation of performing Raman spectroscopic analysis on the skin of the subject. For example, the Raman spectroscopic analysis may be performed by using the measurer MU20 described with reference to FIG. 5 above.

There may be a correlation or functional relation between the fibrous protein (e.g. collagen) and the material relating to a metabolic syndrome (e.g. adiponectin). The operation (S200) of determining the information regarding the material relating to a metabolic syndrome may be performed by using an algorithm based on the correlation or function. The operation (S200) of determining the information regarding the material relating to a metabolic syndrome may be performed by using the processor PU10 described with reference to FIGS. 3 through 7 above. Before noninvasive measuring is performed, the correlation between the fibrous protein (e.g. collagen) and the material relating to a metabolic syndrome (e.g. adiponectin) may be determined, and the algorithm based on the correlation may be prepared. A method of determining the correlation may be the same as described with reference to, for example, FIGS. 11 and 12.

The operation (S300) of outputting the index or numerical value relating to the metabolic syndrome may be performed by using the output device OUT10 described with reference to FIG. 7 above. The noninvasive measuring method may be a metabolic syndrome diagnosis method. However, when information regarding a material other than the material relating to the metabolic syndrome is derived in operation (S200), a purpose of the noninvasive measuring method may be different.

Elements of the apparatuses for noninvasively measuring the bio-analyte (the metabolic syndrome diagnosis apparatus) according to the embodiments, for example, a measurer, a processor, and an output device, may be provided in one device or may be separately provided in two devices or more, which will be explained with reference to FIGS. 14 and 15.

Figure 14:
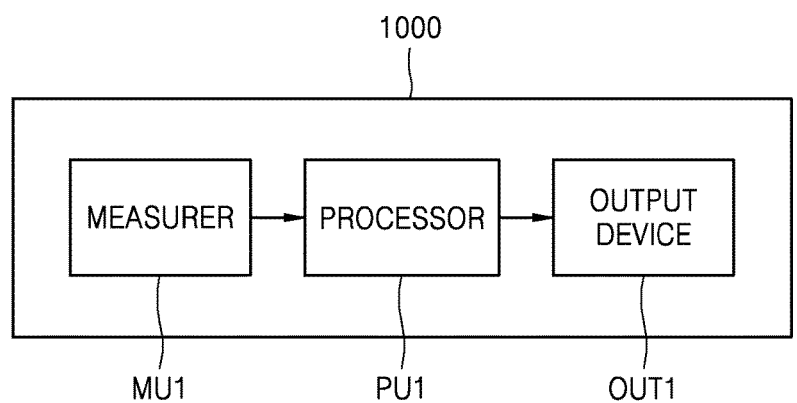
FIG. 14 is a schematic block diagram illustrating an apparatus for noninvasively measuring a bio-analyte according to an exemplary embodiment.

FIG. 14 is a schematic block diagram illustrating an apparatus for noninvasively measuring a bio-analyte according to an exemplary embodiment. Referring to FIG. 14, the apparatus for noninvasively measuring the bio-analyte (hereinafter referred to as the noninvasive measuring apparatus) may include a measurer MU1, a processor PU1, and an output device OUT1 in one device 1000. The measurer MU1, the processor PU1, and the output device OUT1 may be the same as those described with reference to FIGS. 3 through 7.

Figure 15:
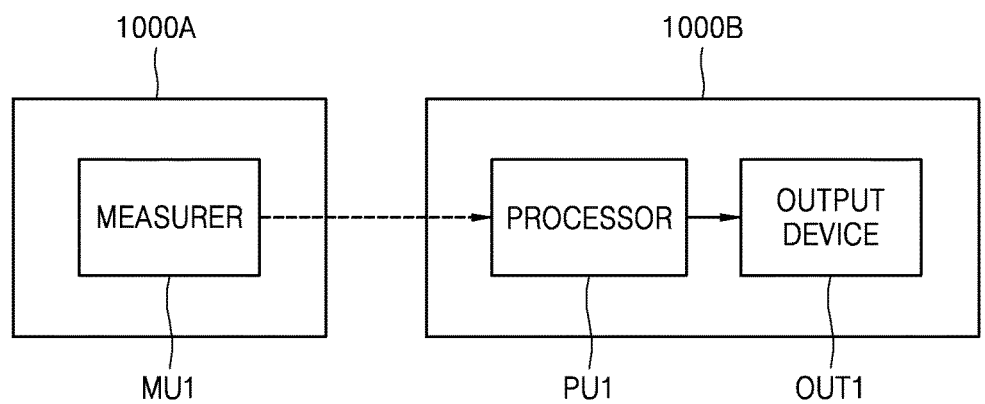
FIG. 15 is a schematic block diagram illustrating an apparatus for noninvasively measuring a bio-analyte according to another exemplary embodiment.

FIG. 15 is a block diagram illustrating an apparatus for noninvasively measuring a bio-analyte according to another exemplary embodiment. Referring to FIG. 15, the apparatus for noninvasively measuring the bio-analyte (hereinafter referred to as the noninvasive measuring apparatus) may include the measurer MU1 in a first device 1000A, and may include the processor PU1 and the output device OUT1 in a second device 1000B. A subject may be measured by the measurer MU1 of the first device 1000, and data obtained by the measurer MU1 may be transmitted to the processor PU1 of the second device 1000B. The measurer MU1 and the processor PU1 may be connected to each other through wireless communication or wired communication. In this connection, a data receiver (not shown) for receiving the data may be further provided in the second device 1000B, and the data receiver may be connected to the processor PU1. Alternatively, the data receiver may be provided in the processor PU1. The data receiver may be referred to as a data obtainer.

Although not shown, according to another exemplary embodiment, a measurer and a processor may be provided in a first device, and an output device may be provided in a second device. In this regard, the processor and the output device may be connected to each other through wireless communication or wired communication. Alternatively, the measurer and a first output device may be provided in the first device, and the processor and a second output device may be provided in the second device. Alternatively, the measurer may be provided in the first device, the processor may be provided in the second device, and the output device may be provided in a third device.

The noninvasive measuring apparatuses of FIGS. 14 and 15 and according to various other exemplary embodiments may be referred to as a noninvasive measuring system. The noninvasive measuring apparatus or the noninvasive measuring system may be applied to small-sized or medium-sized medical devices that are used in public places. The noninvasive measuring apparatus may also be applied in small medical devices and health care devices that are carried by individuals, as well as, in medical devices that are used in hospitals or health examination centers. Also, the noninvasive measuring apparatus or the noninvasive measuring system may be applied to mobile phones and peripheral devices (auxiliary devices) thereof.

Figure 16:
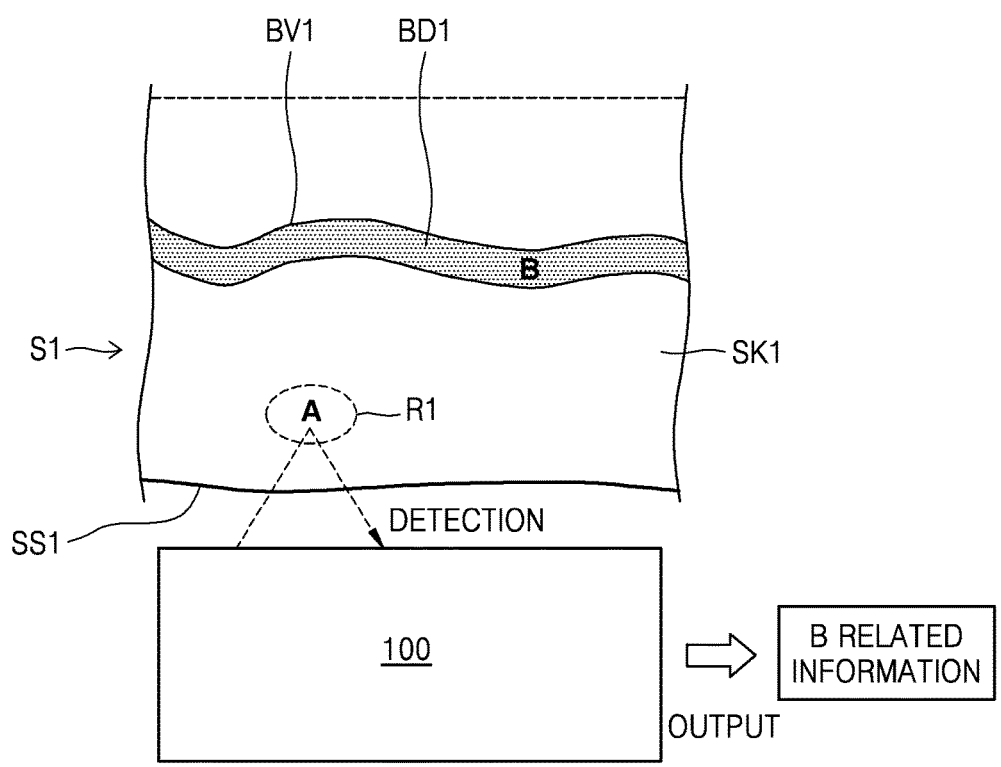
FIG. 16 is a conceptual view illustrating an example where relative positions of a subject and the apparatus for noninvasively measuring the bio-analyte of FIG. 1 are changed.

In addition, although the noninvasive measuring apparatus 100 measures the subject S1 from above the subject S1 in FIG. 1, relative positions of the noninvasive measuring apparatus 100 and the subject S1 may be changed. For example, as shown in FIG. 16, the noninvasive measuring apparatus 100 may measure the subject S1 from below the subject S1. Relative positions of the noninvasive measuring apparatus 100 and the subject S1 may be modified in various other ways.

Although a Raman spectrometer is mainly used to detect a first body part (skin) of a subject in the embodiments described above, a detection method may be different. For example, a near-infrared (NIR) spectrometer may be used to detect the first body part (skin) of the subject. The skin penetration depth of near-infrared ray is relatively greater than that of mid-infrared ray. Therefore, if near-infrared ray is used, not only an epidermis region but also a dermis region may be wholly measured. Thus, the NIR spectrometer may be used as the measurer MU10 of FIGS. 3 and 4. In addition, a light source that generates light having a wavelength that penetrates only the tissue may be used or a filter that selectively filters (or receives) light that is scattered or reflected by the tissue may be used to analyze and quantize an material in tissue of the skin.

Although a first body part (skin) of a subject is mainly detected by using light above, the first body part (skin) of the subject may be detected by using an electrical signal, instead of light. For example, information about the first body part may be obtained by applying an electrical signal (e.g., a low voltage signal) to the first body part and then detecting a change in impedance. One skilled in the art would understand how to adopt metering devices using light, electricity or other emitted stimuli to obtain a response from the skin, which can be measured and correlated. A method of detecting the first body part may be modified in various other ways which would be apparent to one skilled in the art.

The noninvasive measuring apparatus and the noninvasive measuring method (the metabolic syndrome diagnosis apparatus and the metabolic syndrome diagnosis method) described above may be used to very simply examine a subject noninvasively (diagnose a metabolic syndrome). An invasive measuring method that is performed by extracting blood of the subject and measuring and analyzing the extracted blood has disadvantages that the subject feels pain when the blood is extracted and reagents and colorimetric assays that react with a specific material of the blood have to be used when the blood is analyzed. In particular, a reagent and optical equipment for immunoassay is used or mRNA is analyzed to extract blood and measure a concentration of adiponectin. However, according to any exemplary embodiment of the present invention, a target analyte in blood may be accurately (or relatively accurately) measured by analyzing or detecting skin or tissue without extracting blood. Accordingly, various problems or disadvantages of the invasive measuring method may be solved.

In addition, there may be a first comparative method of noninvasively directly detecting an analyte in blood and a second comparative method of detecting a material B in tissue and indirectly measuring the B material in blood. However, the first comparative method has problems that feasibility is low because of complexity in a position and a structure of a blood vessel. The second comparative method has problems that the second comparative method may be used only when the material B in the blood is diffused into tissue and may not be used when a measurement signal of the B material in the tissue is weak. However, the noninvasive measuring apparatus and the noninvasive measuring method according to any of the exemplary embodiments may have higher feasibility, more detectable materials, and a higher (signal to noise ratio) SNR than the first and second comparative methods.

While this inventive concept has been particularly shown and described with reference to exemplary embodiments thereof, it will be understood by one of ordinary skill in the art that various changes in form and details, for example, in the configuration of the non-invasive measuring apparatuses (the noninvasive measuring apparatuses) of FIGS. 1, 3 through 7, and 14 through 16, may be made therein without departing from the spirit and scope of the inventive concept as described by the appended claims and their equivalents. Also, the non-invasive measuring methods (the noninvasive measuring methods) of FIGS. 11 through 13 may also be modified in various ways. Accordingly, the scope of the present inventive concept is not defined by the described embodiments of the present inventive concept but by the technical spirit of the appended claims.

What is claimed is:

1. An apparatus for noninvasively measuring a bio-analyte present in a subject, the apparatus comprising:
    a metering device using spectral characteristics to obtain data comprising information representative of an amount of fibrous protein present in skin of the subject, said spectral characteristic corresponding to wavenumber values in a range of at least one of: 853~857 $cm^{-1}$, 934~938 $cm^{-1}$, 1447~1452 $cm^{-1}$, and 1656~1660 $cm^{-1}$; and
    a processor configured to determine information representative of an amount of an analyte present in blood of the subject based on the obtained information representative of an amount of the fibrous protein, the amount of the analyte being inversely related to the amount of the fibrous protein.

2. The apparatus of claim 1, wherein the metering device is configured to output a measurable characteristic to obtain an amount of collagen in the skin of the subject.

3. The apparatus of claim 2, wherein the metering device is configured to output a measurable characteristic to obtain an amount of type I collagen in the skin of the subject.

4. The apparatus of claim 1, wherein the processor is configured to relate the obtained information representative of the amount of the fibrous protein to the amount of analyte to provide an index of a metabolic syndrome.

5. The apparatus of claim 1, wherein the processor is configured to relate the obtained information representative of the amount of the fibrous protein to an amount of adiponectin.

6. The apparatus of claim 1, wherein the metering device comprises a Raman spectrometer.

7. The apparatus of claim 6, wherein the processor is configured to process data based on a correlation between the fibrous protein and the analyte.

8. The apparatus of claim 1, wherein the metering device comprises a Raman spectrometer configured to obtain the raw data comprising the information representative of an amount of the fibrous protein from the skin of the subject by using the Raman spectrometer.

9. The apparatus of claim 1, wherein the metering device is configured to obtain Raman spectrum data of the skin of the subject and read an intensity value corresponding to at least one wavenumber of a wavenumber range of about 853~857 $cm^{-1}$, 934~938 $cm^{-1}$, 1447~1452 $cm^{-1}$, and 1656~1660 $cm^{-1}$ from the Raman spectrum data to obtain the information about the fibrous protein.

10. An apparatus for diagnosing a metabolic syndrome of a subject comprising:
    a metering device using spectral characteristics to obtain information representative of an amount of a first material present in skin tissue of the subject, said spectral characteristics corresponding to wavenumber values in a range of at least one of: 853~857 $cm^{-1}$, 934~938 $cm^{-1}$, 1447~1452 $cm^{-1}$, and 1656~1660 $cm^{-1}$; and
    a processor configured to determine information regarding an amount of a second material relating to the metabolic syndrome in blood of the subject, based on the information regarding the first material, the amount of the second material being inversely related to the amount of the first material.

11. The apparatus of claim 10, wherein the metering device is configured to output a measurable characteristic to determine an amount of collagen in the skin of the subject.

12. The apparatus of claim 10, wherein the metering device is configured to output a measurable characteristic to obtain an amount of type I collagen in the skin of the subject.

13. The apparatus of claim 10, wherein the processor is configured to relate the obtained information representative of an amount of the first material to an amount of adiponectin.

14. The apparatus of claim 10, wherein the metering device comprises a Raman spectrometer configured to obtain raw data comprising the information representative of an amount of the first material from the skin of the subject.

15. A method of diagnosing a metabolic syndrome, the method comprising:

measuring spectral characteristics to obtain information representative of an amount of fibrous protein from skin of a subject, said spectral characteristics corresponding to a wavenumber values in a range of at least one of: 853~857 $cm^{-1}$, 934~938 $cm^{-1}$, 1447~1452 $cm^{-1}$, and 1656~1660 $cm^{-1}$; and determining information representative of amount of material relating to the metabolic syndrome in blood of the subject based on the representative amount of the fibrous protein, the amount of the material relating to metabolic syndrome being inversely related to the amount of fibrous protein.

16. The method of claim 15, wherein the fibrous protein comprises collagen.

17. The method of claim 16, wherein the collagen comprises type I collagen.

18. The method of claim 15, wherein the material relating to the metabolic syndrome comprises adiponectin.

19. The method of claim 15, wherein the obtained information representative of the amount fibrous protein comprises: performing Raman spectroscopic analysis on the skin of the subject.

20. The method of claim 15, further comprising determining a correlation between the fibrous protein and the material relating to the metabolic syndrome, wherein the determining the information regarding the material relating to the metabolic syndrome comprises: using an algorithm based on the correlation.

21. The method of claim 15, wherein the method is non-invasively performed.

\* \* \* \* \*